(12) United States Patent
Kim

(10) Patent No.: US 10,617,730 B2
(45) Date of Patent: Apr. 14, 2020

(54) COMPOSITION FOR PREVENTING ALOPECIA OR STIMULATING HAIR GROWTH CONTAINING EXTRACELLULAR POLYSACCHARIDE PRODUCED FROM CERIPORIA LACERATA AS ACTIVE INGREDIENT

(71) Applicant: FUGENBIO CO., LTD., Seoul (KR)

(72) Inventor: Yoon Soo Kim, Seongnam-si (KR)

(73) Assignee: FUGENBIO CO., LTD., Seoul (KR)

( * ) Notice: Subject to any disclaimer, the term of this patent is extended or adjusted under 35 U.S.C. 154(b) by 0 days.

(21) Appl. No.: 15/766,632

(22) PCT Filed: Oct. 5, 2016

(86) PCT No.: PCT/KR2016/011140
§ 371 (c)(1),
(2) Date: Apr. 6, 2018

(87) PCT Pub. No.: WO2017/061769
PCT Pub. Date: Apr. 13, 2017

(65) Prior Publication Data
US 2018/0280457 A1 Oct. 4, 2018

(30) Foreign Application Priority Data

Oct. 8, 2015 (KR) ........................ 10-2015-0141411

(51) Int. Cl.
| | | |
|---|---|---|
| *A61K 39/00* | (2006.01) |
| *A61K 39/38* | (2006.01) |
| *A61K 31/74* | (2006.01) |
| *A61K 36/07* | (2006.01) |
| *A61Q 7/00* | (2006.01) |
| *A23L 33/135* | (2016.01) |
| *A61K 8/99* | (2017.01) |
| *A61K 36/06* | (2006.01) |
| *A23L 31/10* | (2016.01) |
| *A23L 31/15* | (2016.01) |
| *A61K 8/9728* | (2017.01) |
| *A61P 17/14* | (2006.01) |

(52) U.S. Cl.
CPC .............. *A61K 36/07* (2013.01); *A23L 31/10* (2016.08); *A23L 31/15* (2016.08); *A23L 33/135* (2016.08); *A61K 8/9728* (2017.08); *A61K 8/99* (2013.01); *A61K 36/06* (2013.01); *A61P 17/14* (2018.01); *A61Q 7/00* (2013.01); *A61K 2236/11* (2013.01); *A61K 2236/17* (2013.01); *A61K 2236/30* (2013.01)

(58) Field of Classification Search
CPC ............................ A61K 39/00; A61K 39/0002
USPC ........ 424/9.1, 9.2, 70.1, 78.02, 184.1, 274.1
See application file for complete search history.

(56) References Cited

FOREIGN PATENT DOCUMENTS

| KR | 10-1031605 B1 | 4/2011 |
|---|---|---|
| KR | 10-2013-0116641 A | 10/2013 |
| KR | 10-1444614 B1 | 9/2014 |
| KR | 10-1522415 B1 | 5/2015 |
| KR | 10-2015-0103690 A | 9/2015 |

OTHER PUBLICATIONS

International Search Report of PCT/KR2016/011140 dated Jan. 5, 2017.

*Primary Examiner* — Rodney P Swartz
(74) *Attorney, Agent, or Firm* — Sughrue Mion, PLLC

(57) ABSTRACT

The present invention relates to extracellular polysaccharide produced from *Ceriporia lacerata*, a mycelium culture medium of *Ceriporia lacerata* containing the extracellular polysaccharide, and a composition for preventing alopecia or stimulating hair growth containing dry powder or an extract of the mycelium culture medium as an active ingredient. The composition according to the present invention inhibits expression of TGF-β and is thus superb in preventing alopecia or stimulating hair growth and a composition containing said composition can be effectively used as a pharmaceutical composition, quasi-drug, healthy functional food and cosmetic composition for preventing alopecia or stimulating hair growth.

17 Claims, 1 Drawing Sheet

[Fig. 1]
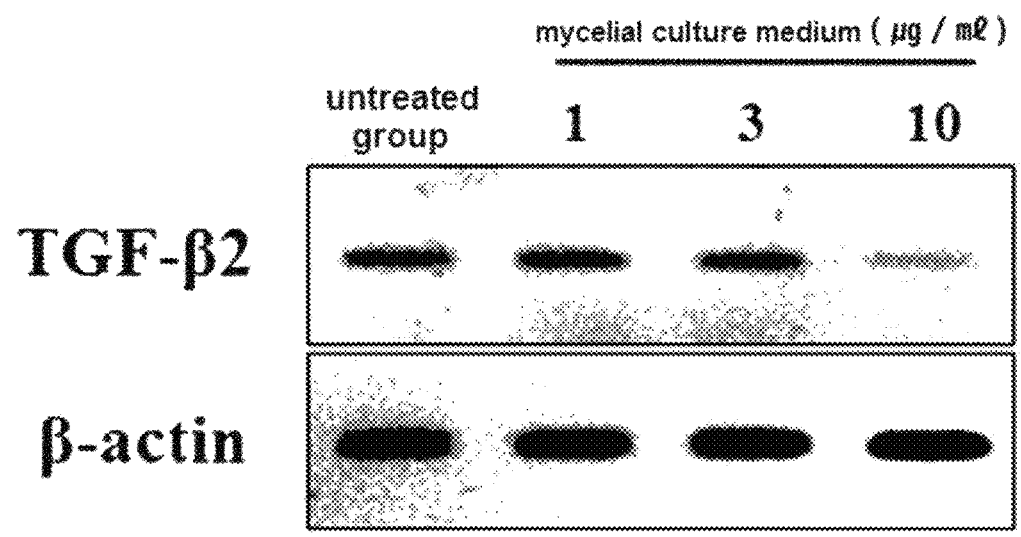
[Fig. 2]
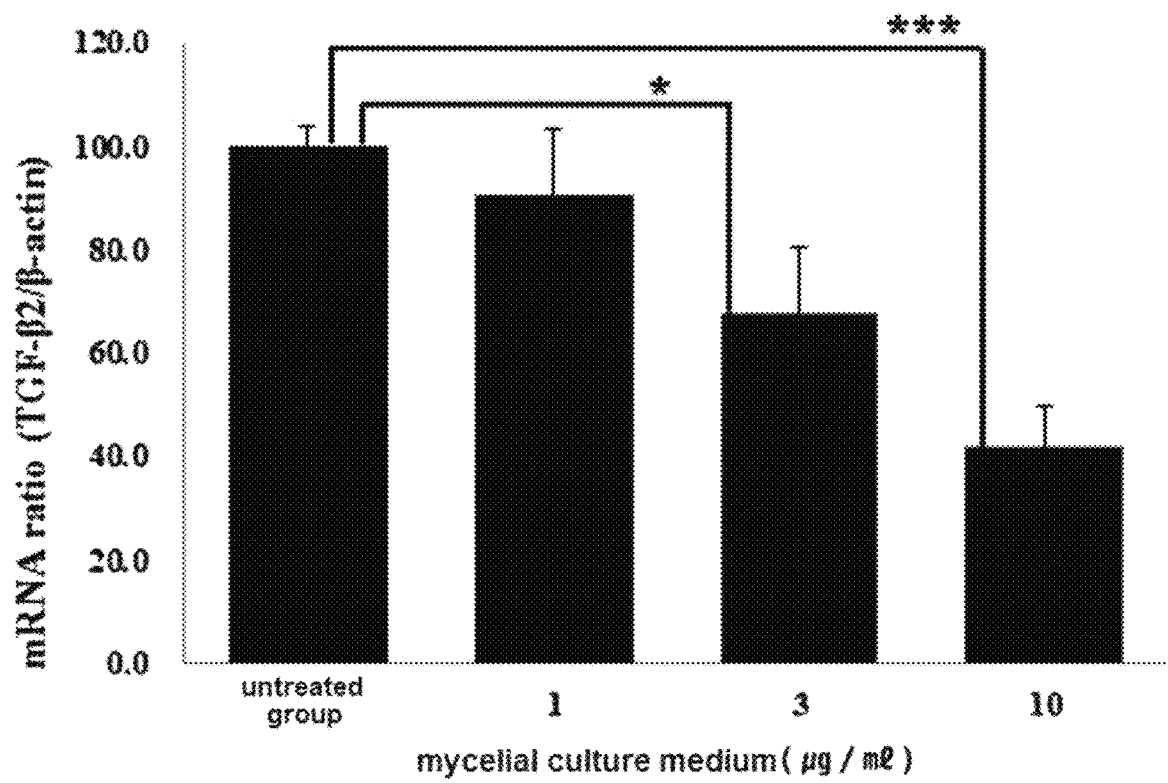

COMPOSITION FOR PREVENTING ALOPECIA OR STIMULATING HAIR GROWTH CONTAINING EXTRACELLULAR POLYSACCHARIDE PRODUCED FROM CERIPORIA LACERATA AS ACTIVE INGREDIENT

CROSS REFERENCE TO RELATED APPLICATIONS

This application is a National Stage of International Application No. PCT/KR2016/011140 filed Oct. 5, 2016, claiming priority based on Korean Patent Application No. 10-2015-0141411 filed Oct. 8, 2015.

TECHNICAL FIELD

The present invention relates to a composition for preventing hair loss or promoting hair growth comprising an active ingredient produced by *Ceriporia lacerata*, a mycelial culture medium of *Ceriporia lacerata* containing the same, dried powders of the mycelial culture medium, or an extract of the mycelial culture medium, as an active ingredient.

BACKGROUND ART

Alopecia, a condition in which hairs are lost from the scalp, is caused by complex involvement of various factors. These factors include internal factors such as genetic constitution, and actions of male hormones, or extrinsic factor such as mental stresses in daily life, and accumulation of lipoperoxides in the scalp. In recent years, not only male pattern hair loss but also hair loss in young ages as well as obesity-induced hair loss are gradually spreading, and many kinds of hair growth agents to improve such hair loss phenomenon are commercially available in the market.

However, most of the hair loss-related technologies intended to prevent hair loss and promote hair growth by controlling male hormones are not effective, and an agent with a definite efficacy have not been developed yet.

In this regard, Korean Patent No. 10-1086504 provides a composition for skin application having the functions of improving blood circulation and dilating blood vessels which contains at least one extract selected from the group of natural extracts consisting of licorice root extract, turmeric extract, grape seed extract, grape seed oil, grapefruit extract, bamboo extract, raspberry extract, cinnamon extract, *Hovenia dulcis* extract, *japonica* extract, alder extract, or mixtures thereof, and it discloses that the above composition for skin application improves blood circulation and dilates blood vessels, thereby improving hair loss symptoms due to the circulatory disturbances in the scalp.

On the other hand, TGF-$\beta$ is a homodimer, which is a multifunctional cytokine that regulates early development, cell cycles, cell proliferation, differentiation, migration and survival, production of extracellular matrix, immune system, angiogenesis, and blood cell production, induction of apoptosis, skeletal formation, and wound healing, etc. in various types of cells and tissues. In addition, vascular endothelial growth factor (VEGF) is a homodimeric glycoprotein that stimulates angiogenesis at the wound site. Also, VEGE is a mitogen which is specific to epithelial cells, and thereby induces epithelial cell migration and proliferation and increases permeability of blood vessels.

It is known that TGF-$\beta$ is secreted morphologically during apoptosis in the catagen phase, and hair loss develops rapidly due to such substances. Therefore, it is necessary to reduce the process of progression from a normal hair state to alopecia by inhibiting TGF-$\beta$ expression, which results in delaying of hair loss.

Meanwhile, it is known that *Ceriporia lacerata* is a kind of white-rotting fungus and conducts co-metabolism, i.e., lignin decomposition, in order to use carbon sources such as cellulose, hemi-cellulose, other polysaccharides, and glycerol, etc., in the ecosystem.

Regarding the use of *Ceriporia lacerata* in medical treatment, only the use of the extract of the culture medium of *Ceriporia lacerata* disclosed in Korean Patent No. 10-1031605 in the treatment of in diabetes is known so far. However, it has not been reported that *Ceriporia lacerata* has the effect of preventing hair loss or promoting hair growth yet.

DISCLOSURE OF INVENTION

Technical Problem

Accordingly, the present inventors have found that an active ingredient produced by *Ceriporia lacerata*, a mycelial culture medium of *Ceriporia lacerata* containing the active ingredient, or dried powders or an extract of the mycelial culture medium exhibits the effect of preventing hair loss or promoting hair growth, and have completed the present invention.

It is an object of the present invention to provide a composition, a pharmaceutical composition, a quasi-drug, a health functional food and a cosmetic composition for preventing hair loss or promoting hair growth, which contain an active ingredient produced by *Ceriporia lacerata*.

It is another object of the present invention to provide a method for preventing hair loss or promoting hair growth using an active ingredient produced by *Ceriporia lacerata*.

It is still another object of the present invention to provide a use of an active ingredient produced by *Ceriporia lacerata* for the preparation of a composition for preventing hair loss or promoting hair growth.

Solution to Problem

In accordance with one object of the present invention, there is provided a composition, a pharmaceutical composition, a quasi-drug, a health functional food, and a cosmetic composition for preventing hair loss or promoting hair growth, which contain an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium, as an active ingredient.

In accordance with another object of the present invention, there is provided a method for preventing hair loss or promoting hair growth comprising administering an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium, to a subject in need thereof.

In accordance with still another object of the present invention, there is provided a use of an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium, for the preparation of a composition for preventing hair loss or promoting hair growth Advantageous Effects of Invention A composition for preventing hair loss or promoting hair growth of the present invention comprising an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium, as an active ingredient, inhibits TGF-β expression, thereby reducing the process of progression from a normal hair state to alopecia, and thus has an excellent effect of delaying hair loss. Therefore, the above composition can be utilized as a pharmaceutical composition, a quasi-drug, a health functional food, or a cosmetic composition for preventing hair loss or promoting hair growth.

BRIEF DESCRIPTION OF DRAWINGS

FIG. 1 shows the result of electrophoresis of the RT-PCR products of a human hair-forming cell line treated with the mycelial culture medium of *Ceriporia lacerata* at various concentrations.

FIG. 2 shows the result of quantification of the RT-PCR products of a human hair-forming cell line treated with the mycelial culture medium of *Ceriporia lacerata* at various concentrations.

BEST MODE FOR CARRYING OUT THE INVENTION

Hereinafter, the present invention is described in detail.

There is provided a composition for preventing hair loss or promoting hair growth, which contains an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium, as an active ingredient.

As used herein, the term "extracellular polysaccharide (EPS)" refers to a part of the cell wall of a microorganism such as fungi, which means a polysaccharide secreted extracellularly to form a capsule therearound, or a substance secreted as mucilage around cells or into media. The extracellular polysaccharide is secreted by microorganisms to protect themselves from the external environment such as antibodies, toxic substances, protozoa, and bacteriophages, etc.

In the above composition, the extracellular polysaccharide may comprise 40 to 60 wt % of sugar and 30 to 40 wt % of protein, 40 to 50 wt % of sugar and 32 to 38 wt % of protein, or 43 to 47 wt % of sugar and 33 to 36 wt % of protein, specifically about 45 wt % of sugar and about 34 wt % of protein.

The sugar may include mannose, galactose and glucose.

The extracellular polysaccharide may have a molecular weight of 100 to 150 kDa, 110 to 140 kDa or 115 to 125 kDa, more specifically about 120 kDa.

According to one embodiment of the present invention, the extracellular polysaccharide may be prepared by a preparation method comprising the steps of: (a) culturing mycelia of *Ceriporia lacerata* in a liquid to prepare a mycelial culture medium of *Ceriporia lacerata*, (b) drying the mycelial culture medium of *Ceriporia lacerata* to form powders, and (c) extracting the dried powders of the mycelial culture medium of *Ceriporia lacerata* with a solvent, and filtering and concentrating the resultant extract under reduced pressure.

The medium for culturing in a liquid in the step (a) may contain sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water, and the hydrogen ion concentration (pH) of the medium may be 4.5 to 6.0.

As a specific example, the medium may contain 0.2 to 3 wt % of sugar, 0.2 to 3 wt % of glucose, 0.2 to 4 wt % of starch, 0.1 to 0.5 wt % of sorghum powder, 0.1 to 0.5 wt % of barley powder, 0.2 to 3 wt % of soybean flour, 0.01 to 0.1 wt % of magnesium sulfate ($MgSO_4$), 0.01 to 0.25 wt % of monopotassium phosphate ($KH_2PO_4$), 0.01 to 0.25 wt % of dipotassium phosphate ($K_2HPO_4$) and residual quantity of water.

The culture in a liquid of the step (a) may be conducted under a blue LED light source, with a carbon dioxide concentration maintained at 1,000 to 2,000 ppm.

The culture in a liquid, for example, may be conducted for 8 to 13 days at 20 to 25° C., under a blue LED light source, with the pH maintained at 4.5 to 6.0, an illuminance maintained at 0.1 to 0.8 LUX, an air injected at 0.5 to 2.0 $kgf/cm^2$, a carbon dioxide concentration maintained at 1,000 to 2,000 ppm. Specifically, the culture may be conducted under the condition of 20 to 25° C., pH 4.5 to 6.0, 0.5 to 2.0 $kgf/cm^2$, and 1,000 to 2,000 ppm for 5 to 15 days. Culturing in a liquid under the above condition is preferable since it leads to a high content of an extracellular polysaccharide produced.

The parent strain for use in step (a) may be a strain obtained by culturing a dominant strain stored in PDA (Potato dextrose agar) medium at 1 to 5° C., in PDB (Potato dextrose broth) medium in Erlenmeyer flask using a shaking incubator at a temperature maintained at about 25° C. for 7 to 9 days. In addition, the culture medium or mycelium obtained after culturing the parent strain as described above can be used as an inoculum. Specifically, the amount of the mycelia to be inoculated may be about 0.5% (w/v) based on the solution to be cultured. Since a high amount of the mycelia (%/100 mL, w/v) does not necessarily result in a high content of the extracellular polysaccharide, the medium composition may be preferably selected such that it provides a condition for maximizing the content of extracellular polysaccharide, rather than the best nutritional ratio and environmental condition for the growth of mycelia.

The culture medium may be separated and purified into mycelia and an aqueous solution. For the separation and purification, the mycelia may be eliminated from the culture medium using a centrifuge and the remaining solution may be repeatedly purified using a Multi-Sheet Filter Press and a vibrating membrane separator (PALLSEP), followed by irradiation with UV rays for 1 minute. Also, the culture medium may be sealed and stored after removing oxygen, since the presence of mycelia in the medium may result in the change in the content of the effective ingredient due to the growth of the mycelia.

In the step (b), the mycelial culture medium prepared in the step (a) may be dried to form powders. In order to prevent the loss of an effective substance, the drying may be carried out at a temperature of 40° C. or lower, more specifically 30° C. or lower, for 48 to 96 hours. In addition, it is preferable that the drying is conducted using a vacuum freeze dryer rather than a vacuum dryer in which a relatively high evaporation temperature is set, in terms of minimizing the change in the content of the effective substance.

In the step (c), after the dried powders of a mycelial culture medium obtained in the step (b) are extracted with a solvent, an extracellular polysaccharide, an active ingredient according to the present invention, is isolated.

Specifically, 100 ml of distilled water was added to 3 to 10 g of the dried powders of the mycelial culture medium and suspended well, followed by centrifugation at 5,000 to 10,000 rpm for 10 to 30 minutes to obtain a supernatant. And, then, a 2-to 3-fold amount of extraction solvent may be added to the supernatant, which may then be placed in a refrigerator at 1 to 5° C. and allowed to stand for 10 to 15 hours. The supernatant in the solution which had been allowed to stand may be obtained and centrifuged again at 5,000 to 10,000 rpm for 10 to 30 minutes, and the precipitate may be recovered, thereby preparing a crude extracellular polysaccharide. The crude extracellular polysaccharide may be vacuum freeze-dried at 30° C. or lower to obtain an extracellular polysaccharide.

The extraction solvent may be a solvent selected from the group consisting of water, a lower alcohol having 1 to 4 carbon atoms, acetone, ether, chloroform and ethyl acetate or a mixture thereof, and more specifically, it may be a solvent selected from the group consisting of water, methanol, ethanol, butanol, acetone, and ethyl acetate or a mixture thereof, even more specifically, water or 50 to 80% (v/v) aqueous solution of ethanol.

A composition for preventing hair loss or promoting hair growth of the present invention inhibits TGF-β expression, thereby reducing the process of progression from a normal hair state to alopecia, and thus has the effect of delaying hair loss and promoting hair growth.

A composition for preventing hair loss or promoting hair growth of the present invention containing an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium can be used as an additive comprised in a pharmaceutical composition, a quasi-drug, a health functional food, and a cosmetic composition for the purpose of exhibiting the effect of preventing hair loss or promoting hair growth. Herein, the dosage and the dosage form can be adequately adjusted according to a preparation purpose.

The extracellular polysaccharide may be comprised in a composition for preventing hair loss or promoting hair growth in an amount of 0.1 to 80 wt %, specifically 0.1 to 50 wt %, based on the total weight of the composition. And the composition for preventing hair loss or promoting hair growth may comprise a mycelial culture medium of *Ceriporia lacerata*, dried powders thereof or an extract of the mycelial culture medium in an amount which corresponds to the above amount of the extracellular polysaccharide. However, more specifically, the effective content of an extracellular polysaccharide, a mycelial culture medium containing the extracellular polysaccharide, or dried powder, or an extract of the mycelial culture medium may be adequately adjusted according to the method of use and purpose of the composition.

Also, the present invention provides a pharmaceutical composition for preventing hair loss or promoting hair growth comprising an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium, as an active ingredient.

Such extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium is as described above.

A pharmaceutical composition of the present invention inhibits TGF-β expression, thereby has the effect of reducing the process of progression from a normal hair state to alopecia.

The above pharmaceutical composition may further comprise suitable carriers, excipients and diluents conventionally used in pharmaceutical compositions as well as comprising an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium, as an active ingredient.

The pharmaceutical composition according to the present invention may be formulated according to a conventional method. Suitable formulations include, but are not limited to, tablets, pills, powders, granules, sugarcoated pills, hard or soft capsules, solutions, suspensions or emulsions, injections, suppositories, and the like.

The pharmaceutical composition according to the present invention can be prepared into a suitable formulation using a pharmaceutically inert organic or inorganic carrier. That is, if the formulation is a tablet, a coated tablet, a sugar-coated tablet or a hard capsule, lactose, sucrose, starch or a derivative thereof, talc, calcium carbonate, gelatin, or stearic acid or a salt thereof may be used. Also, if the formulation is a soft capsule, vegetable oil, wax, fat, or semi-solid or liquid polyol may be used. Furthermore, if the formulation is a solution or syrup, water, polyol, glycerol, vegetable oil, and/or the like may be used.

A pharmaceutical composition according to the present invention may further comprise a preservative, a stabilizer, a humectant, an emulsifier, a solubilizer, a sweetener, a coloring agent, an osmotic pressure regulator, an antioxidant, and the like in addition to the above carrier.

A method of administering a pharmaceutical composition according to the present invention can be easily selected in accordance with the formulation, which may be oral or parenteral administration. The dosage of the extracellular polysaccharide, an active ingredient, may vary depending on the patient's age, sex, weight, disease severity, and route of administration, but is generally in the range of 5 to 500 mg/kg, specifically 10 to 250 mg/kg, which may be administered in one to three divided doses a day. However, such dosage does not limit the scope of the present invention.

A pharmaceutical composition according to the present invention not only provides an excellent effect of preventing hair loss and/or promoting hair growth, but also shows little toxicity and adverse events, and thus can be safely used by long-term administration.

In addition, the present invention provides a quasi-drug for preventing hair loss or promoting hair growth, which contains an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium, as an active ingredient.

Such extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium is as described above.

The quasi-drug of the present invention can be formulated in any form if an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium can be mixed in the quasi-drug. Specifically, the quasi-drug may be formulated in various forms such as solutions, sol-gels, emulsion, oil, waxes, aerosols, etc., which may be hair tonics, hair creams, hair lotions, hair shampoos, hair rinses, hair conditioners, hair sprays, hair aerosols, pomades, gels, hair packs, hair treatments, eyebrow hair growth agents, eyelash hair growth agents, or eyelash nutrients, etc. Also the quasi-drug of the present invention can be used for the production or processing of scalp or hair devices such as wigs or hats. In addition, the quasi-drug may contain various ingredients mixed in a conventional a composition for preventing hair loss in accordance with the above-described various formulations or its final purpose. For example, in the case of a shampoo formulation, it may contain at least one of a synthetic surfactant as a cleaning agent and a preservative, a thickener, a viscosity regulator, a pH adjuster, a perfume, a dye, a hair conditioner and water.

In addition, the present invention provides a health functional food for preventing hair loss or promoting hair growth, which contains an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium, as an active ingredient.

Such extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium is as described above.

A health functional food according to the present invention may be in the form of powders, granules, a tablet, a capsule or a drink, which may be a candy, a chocolate, a drink, a gum, a tea, a vitamin complex, a health supplementary food, etc.

Herein, the content of an extracellular polysaccharide, a mycelial culture medium containing the same, dried powders of the mycelial culture medium, or an extract of the mycelial culture medium according to the present invention comprised in the health functional food may be generally in the range of 0.01 to 50 wt %, specifically 0.1 to 20 wt % based on the weight of the entire health functional food. Also, in the case of a drink, it may be comprised in the amount of 0.02 to 10 g, specifically 0.3 to 1 g based on 100 mL of the drink.

The health functional food may further comprise a sitologically acceptable food supplementary additive in addition to an extracellular polysaccharide, a mycelial culture medium of *Ceriporia lacerata* containing the same, dried powders of the mycelial culture medium, or an extract of the mycelial culture medium of the present invention.

Also, the present invention provides a cosmetic composition for preventing hair loss or promoting hair growth, which contains an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium, as an active ingredient.

The cosmetic composition may comprise general supplements and carriers conventionally included in cosmetics, for example, stabilizers, solubilizers, surfactants, vitamins, pigments and flavoring agents in addition to an exopolysaccharide a mycelial culture medium of *Ceriporia lacerata* containing the exopolysaccharide, dried powders of the mycelial culture medium, or an extract of the mycelial culture medium, which is an active ingredient showing the effect of preventing hair loss or promoting hair growth.

The cosmetic composition may be prepared into any formulations conventionally produced in the art, for example, a solution, a suspension, an emulsion, a paste, a gel, a cream, a lotion, powders, a soap, a surfactant-containing cleansing, oil, a powder foundation, an emulsion foundation, a wax foundation or a spray. More specifically, it can be prepared into a formulation such as a shampoo, a rinse, a hair essence, a hair nutrient, a hair serum, a hair massage cream, a hair lotion, a hair pack or a hair spray, but is not limited thereto.

Further, the present invention provides a method for preventing hair loss or promoting hair growth comprising administering an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium described above to a subject in need thereof. Herein, the subject may be a mammal, specifically, a human.

Further, the present invention provides a use of an extracellular polysaccharide produced by *Ceriporia lacerata*, a mycelial culture medium of *Ceriporia lacerata* containing the extracellular polysaccharide, dried powders of the mycelial culture medium, or an extract of the mycelial culture medium described above, for the preparation of a composition for preventing hair loss or promoting hair growth.

MODE FOR THE INVENTION

Hereinafter, the present invention is explained in detail by Examples. The following Examples are intended to further illustrate the present invention without limiting its scope.

EXAMPLES

Preparation Example 1. Preparation of Mycelial Culture Medium of *Ceriporia lacerata*, Dried Powders Thereof, Extract, and Extracellular Polysaccharide (Exopolysaccharide, Hereinafter, Referred to as "EPS")

1-1: Preparation of Mycelial Culture Medium of *Ceriporia lacerata*

*Ceriporia lacerata* isolated from *Quercus serrata* collected at Sangju city, Gyeongbuk province were subcultured to obtain a parent strain, which was subsequently freeze-stored at −80° C., and the freeze-stored strain was cultured with 2 to 3 passages in PDA (Potato dextrose agar) medium (87 plastic bulbs, Difco, Becton Dickinson and Company), and the complete strains with sufficient numbers (hereinafter referred to as "PDA culture strain") were selected and stored in a refrigerator at 4° C. until use. Then, 600 mL of the PDB (Potato dextrose broth) medium (Difco, Becton Dickinson and Company) was placed in an Erlenmeyer flask, and then a PDA culture strain was added thereto and shake-cultured at 25° C. for 8 days to obtain a PDB culture strain.

Meanwhile, for the culture of the strain, a liquid culture medium containing 1.5 wt % of sugar, 0.5 wt % of glucose, 0.5 wt % of potato starch, 0.25 wt % of sorghum powder, 0.25 wt % of barley powder, 0.75 wt % of soybean flour, 0.05 wt % of magnesium sulfate ($MgSO_4$), 0.05 wt % of monopotassium phosphate ($KH_2PO_4$), 0.05 wt % of dipotassium phosphate ($K_2HPO_4$) and residual quantity of water was sterilized for 20 minutes at 121° C. in a 800 L fermenter with the air injected at 1.5 kgf/cm². Then, the medium was cooled to 23° C., and inoculated with 600 mL of the PDB culture strain as a starter, and *Ceriporia lacerata* mycelia were liquid-cultured in the medium for 10 days at a constant temperature of 23° C., under a blue LED light source, with the air injected at 0.5 to 1.5 kgf/cm², an illuminance of 0.5 LUX, and a carbon dioxide concentration of 2,000 ppm, to prepare the mycelial culture medium of *Ceriporia lacerata*.

1-2: Preparation of Dried Powders of Mycelial Culture Medium of *Ceriporia lacerata*

The mycelial culture medium of *Ceriporia lacerata* prepared in the Preparation Example 1-1 was vacuum freeze-dried by using a vacuum freeze dryer at 25° C. for 72 hours to form powders, to prepare dried powders of a mycelial culture medium of *Ceriporia lacerata*.

1-3: Preparation of Extract of Mycelial Culture Medium of *Ceriporia lacerata*

5 g of dried powders of the mycelial culture medium of *Ceriporia lacerata* prepared in Preparation Example 1-2 was added to 100 mL of distilled water and sufficiently suspended, and then the resulting solution was centrifuged at 8,000 rpm for 20 minutes. And then the supernatant separated therefrom was mixed with a 2-to 3-fold amount of ethanol, and allowed to stand for 12 hours at 4° C. Thereafter, the resultant supernatant was taken and an extract of the mycelial culture medium of *Ceriporia lacerata* was prepared therefrom.

1-4: Preparation of EPS From Extract of Mycelial Culture Medium of *Ceriporia lacerata*

The extract of the mycelial culture medium of *Ceriporia lacerata* prepared in Preparation Example 1-3 was further centrifuged at 8,000 rpm for 20 minutes, and then the precipitate was recovered to obtain crude EPS. The crude EPS was vacuum freeze-dried by using a vacuum freeze dryer at 25° C. for 72 hours to obtain an EPS produced by *Ceriporia lacerata*.

Example 1. Evaluation of EPS Properties 1-1: Molecular Weight Measurement of EPS Using Gel Permeation Chromatography (GPC)

The EPS prepared in Preparation Example 1 was dissolved in a solution of 0.1 M $Na_2SO_4$/0.05 M $NaN_3$ (adjusted to pH 4 with glacial acetic acid) to a concentration of 1% (w/v), and then the mixture was centrifuged at 4,000 rpm for 0.5 hour, then the supernatant alone was isolated and filtered with a 0.45 μm syringe filter and analyzed by GPC.

Specifically, as for the GPS analysis condition, a refractive index of the detector was used and OHpak SB 805 HQ (Shodex, Japan) was used for the GPC column, and 0.1 M $Na_2SO_4$/0.05 M $NaN_3$ (adjusted to pH 4 with glacial acetic acid) was used for the mobile phase, which was allowed to flow at a flow rate of 1.0 mL/min. Standard curves were generated using dextrans (American Polymer Corporation, USA) of different molecular weights (130 kDa, 400 kDa, 770 kDa or 1200 kDa), and the molecular weight of EPS was measured using refractive index (RI) measuring instrument Knauer K-2310 (Germany). The measurement conditions are summarized in Table 1 below.

TABLE 1

| | Measurement of molecular weight |
|---|---|
| HPLC system | Knauer K-501 system |
| Column | OHpak SB 805 HQ (Shodex, Japan) |
| Mobile phase | 0.1M $Na_2SO_4$/0.05M $NaN_3$/pH 4 |
| Flow rate | 1.0 mL/min |
| Measuring instrument | RI (Knauer K-2310) |

As a result, the molecular weight of EPS of the present invention was about 120 kDa.

1-2: Measurement of Sugar and Protein Contents of EPS

The EPS prepared in Preparation Example 1 was subjected to secondary purification and treated with a protein-hydrolysis enzyme to measure sugar and protein contents.

Specifically, the primary-purified EPS (EPS prepared in Preparation Example 1) was dissolved in distilled water and centrifuged at 8,000 rpm for 20 minutes to separate the supernatant, and then a 2-to 3-fold amount of ethanol was added thereto. The mixture was placed in a refrigerator at 4° C. and allowed to stand for 12 hours. Thereafter, the resultant supernatant alone was centrifuged again at 8,000 rpm for 20 minutes, and the precipitate was recovered to obtain a secondary-purified EPS. And the secondary-purified EPS was dissolved in distilled water and treated with alcalase, a protein-hydrolysis enzyme, at a concentration of 0.5% (w/v) at 50° C. for 30 minutes.

The sugar content was measured by the phenol-sulfuric acid method. Specifically, 25 μL of 80% (w/v) phenol was added to 1 mL of each of the samples diluted at various concentrations, and then 2.5 mL of sulfuric acid was added thereto. The mixture was cooled to room temperature, and then the sugar content was calculated by measuring the absorbance at 465 nm.

Also, the protein content was measured by BCA method (see Smith P K et al., *Analytical Biochemistry*, 150 (1): 76-85, 1985) and bovine serum albumin was used as a standard.

The sugar contents and protein contents measured as described above are shown in Table 2 below. The sugar content was 45 to 51 wt % and the protein content was 33 to 34 wt %.

TABLE 2

| | Yield (%) | Total sugar content (%) | Total protein content (%) |
|---|---|---|---|
| EPS | 1.22 ± 0.03 | 45.32 ± 1.41 | 34.17 ± 0.73 |
| Secondary-purified EPS | 0.78 ± 0.01 | 50.49 ± 0.52 | 33.50 ± 2.79 |
| Enzyme-treated EPS* | 0.24 ± 0.06 | 51.39 ± 1.32 | 34.61 ± 1.51 |

*Enzyme treatment: alkalase 0.5%, 50° C., 30 minutes.
Each value represents mean ± SE (n ≥ 3).

Also, as the result of analyzing sugar composition of EPS, it was found that the EPS mainly contains mannose, galactose and glucose.

Example 2. Measurement of Inhibitory Effect on TGF-μ2 Expression

In order to evaluate the hair loss-preventing effect of dried powders of the mycelial culture medium of *Ceriporia lacerata* of Preparation Example 1.2, aqueous solutions were prepared by dissolving dried powders of the mycelial culture medium of *Ceriporia lacerata* in distilled water at various concentrations, and were added to the human hair-forming cell line, and the expression level of TGF-β2 was measured.

Specifically, the human hair-forming cell line [HaCaT; purchased from CLS (Cell Lines Service GmbH, Eppelheim, Germany)] was placed in the wells of 96 well plate containing DMEM (Dulbecco's modified eagle medium, Gibco BRL, Gibco Island, N.Y.) supplemented with 5% fetal bovine serum (FBS) (Gibco BRL, Gibco Island, N.Y.) and 1% antibiotic antimycotic solution (Gibco BRL, Gibco Island, N.Y.), and then cultured in an incubator at a condition of 37° C. and 5% $CO_2$ for 3 days. Thereafter, 200 μl of DMEM of each well was treated with 2 μl of a sample solution, which was then cultured in an incubator at a condition of 37° C. and 5% $CO_2$ for 24 hours. The sample solution was an aqueous solution prepared by dissolving the dried powders of the mycelial culture medium of *Ceriporia lacerata* of Preparation Example 1.2 in distilled water at the concentration of 1 μg/ml, 3 μg/ml or 10 μg/ml. And a control group was not treated with dried powders of the mycelial culture medium of *Ceriporia lacerata*.

Then, pre-RNA was isolated using the easy-BLUE™ Total RNA Extraction kit (iNtRON Biotechnology Inc., Seoul, Korea) according to the manufacturer's instructions, and the isolated pre-RNA (1 μg) was reverse transcribed into cDNA using commercially available Accupower® RT pre-Mix (Bioneer, Daejeon, Korea). The cDNA was amplified using Accupower® PCR Premix (Bioneer, Daejeon, Korea) and the primers specific for mRNA of TGF-β2 and β-actin (Cho H R, etc., *J. Korean Med. Sci.*, 2004, 19, 853-858). Specifically, reverse transcription PCR (RT-PCR) was performed by repeating a set of reactions (a predenaturation step at 95° C. for 4 minutes, a denaturation step at 95° C. for 1 minute, an annealing step at 55° C. for 1 minute, an elongation step at 72° C. for 5 minutes, and a post-elongation step at 72° C. for 5 minutes) for 30 cycles. The PCR product was electrophoresed on 1% agarose gel and the relative mRNA expression level based on β-actin mRNA was quantified using the Quantity One software. The electrophoresis results of the PCR products are shown in FIG. 1, and the quantification results are shown in FIG. 2.

As shown in FIG. 1 and FIG. 2, compared with the untreated group, the cells treated with 3 μg/ml of the mycelial culture medium of *Ceriporia lacerata* of the present invention showed a significantly decreased TGF-β2 expression level of 67.6%, and the cells treated with 10 μg/ml of the above mycelial culture medium showed a significantly decreased TGF-β2 expression level of 42.1%. Thus, it was found that the mycelial culture medium of *Ceriporia lacerata* of the present invention inhibits TGF-β expression in a concentration-dependent manner, thereby preventing hair loss and promoting hair growth.

The invention claimed is:

1. A method for preventing hair loss and/or promoting hair growth, comprising administering an effective amount of a composition containing at least one of (i)-(iii):
   (i) a mycelial culture medium of *Ceriporia lacerata* containing an extracellular polysaccharide produced by the *Ceriporia lacerata*,
   (ii) dried powders of the mycelial culture medium of *Ceriporia lacerata* of (i), and
   (iii) an extract of the mycelial culture medium of *Ceriporia lacerata* of (i),
as an active ingredient, to a subject in need thereof.

2. The method of claim 1, wherein the extracellular polysaccharide produced by *Ceriporia lacerata* contains mannose, galactose and glucose.

3. The method of claim 1, wherein the extract of the mycelial culture medium of (iii) is prepared by a method comprising:
   (a) culturing the mycelia of *Ceriporia lacerata* in a liquid to prepare a mycelial culture medium of *Ceriporia lacerata*,
   (b) drying the mycelial culture medium of *Ceriporia lacerata* to form powders, and
   (c) extracting the dried powders of the mycelial culture medium of *Ceriporia lacerata* with a solvent.

4. The method of claim 3, wherein the liquid of step (a) comprises a medium which comprises sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water, and the hydrogen ion concentration of the medium is pH 4.5 to 6.0.

5. The method of claim 3, wherein the step (a) of culturing in a liquid is conducted under a blue LED light source with a carbon dioxide concentration maintained at 1,000 to 2,000 ppm.

6. The method of claim 1, wherein the extracellular polysaccharide is comprised in an amount of 0.1 to 80 wt % based on the total weight of the composition.

7. The method of claim 1, wherein the composition inhibits TGF-β production.

8. The method of claim 1, wherein the composition is a pharmaceutical composition.

9. The method of claim 8, wherein the pharmaceutical composition is administered orally or parenterally.

10. The method of claim 1, wherein the composition is in a formulation selected from the group consisting of a hair tonic, a hair cream, a hair lotion, a hair shampoo, a hair rinse, a hair conditioner, a hair spray, a hair aerosol, a pomade, a gel, hair mask pack, a hair treatment, an eyebrow hair growth agent, an eyelash hair growth agent, and an eyelash nutrient agent.

11. The method of claim 1, wherein the composition is a foodstuff.

12. The method of claim 11, wherein the foodstuff is in a form selected from the group consisting of powders, granules, a tablet, a capsule, a drink, a chewable gum, a tea, a vitamin complex, and a health supplementary food.

13. The method of claim 1, wherein the composition is a cosmetic composition.

14. The method of claim 1, wherein the composition is a hair-care product.

15. The method of claim 14, wherein the hair-care product is in a formulation selected from the group consisting of a shampoo, a rinse, a hair essence, a hair nutrient, a hair serum, a hair massage cream, a hair lotion, a hair mask pack, and a hair spray.

16. The method of claim 1, wherein the subject is a mammal.

17. A method for inhibiting TGF-β production in a subject, comprising administering an effective amount of a composition containing at least one of (i)-(iii):
   (i) a mycelial culture medium of *Ceriporia lacerata* containing an extracellular polysaccharide produced by the *Ceriporia lacerata*,
   (ii) dried powders of the mycelial culture medium of *Ceriporia lacerata* of (i), and
   (iii) an extract of the mycelial culture medium of *Ceriporia lacerata* of (i),
as an active ingredient, to the subject.

* * * * *